US006922584B2

(12) United States Patent
Wang et al.

(10) Patent No.: US 6,922,584 B2
(45) Date of Patent: Jul. 26, 2005

(54) METHOD AND APPARATUS FOR DISCRIMINATION ATRIAL FIBRILLATION USING VENTRICULAR RATE DETECTION

(75) Inventors: Li Wang, White Bear Lake, MN (US); Mark L. Brown, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 495 days.

(21) Appl. No.: 09/998,553

(22) Filed: Nov. 28, 2001

(65) Prior Publication Data

US 2002/0065473 A1 May 30, 2002

Related U.S. Application Data

(60) Provisional application No. 60/253,553, filed on Nov. 28, 2000.

(51) Int. Cl.[7] .............................................. A61B 5/0452
(52) U.S. Cl. ........................................ 600/515; 600/518
(58) Field of Search ................................ 600/508–510, 600/515–516, 518, 519, 521, 523; 607/4, 9, 14, 17, 25

(56) References Cited

U.S. PATENT DOCUMENTS

| 4,587,976 A | 5/1986 | Schmid et al. ............... 128/699 |
| 4,726,380 A | 2/1988 | Vollmann et al. ............ 128/419 |
| 4,947,858 A | 8/1990 | Smith .......................... 128/696 |
| 5,048,521 A | 9/1991 | Pless et al. .................. 128/419 |
| 5,058,599 A | 10/1991 | Andersen et al. ............ 128/705 |
| 5,086,772 A | 2/1992 | Larnard et al. ............... 128/419 |
| 5,107,850 A | 4/1992 | Olive ........................... 128/705 |
| 5,111,396 A | 5/1992 | Mills et al. .............. 364/413.06 |
| 5,161,527 A | 11/1992 | Nappholz et al. ............ 128/419 |
| 5,193,535 A | 3/1993 | Bardy et al. ................. 128/419 |
| 5,205,583 A | 4/1993 | Henseler et al. ............. 280/743 |

(Continued)

FOREIGN PATENT DOCUMENTS

| EP | 0 617 980 A2 | 5/1994 | .......... A61N/1/368 |
| WO | WO 98/02209 | 1/1998 | .......... A61N/1/375 |
| WO | WO 00/51680 | 8/2000 | ............ A61N/1/37 |

OTHER PUBLICATIONS

Tateno et al., A Method for Detection of Atrial Fibrillation Using RR Intervals, Computers in Cardiology 2000, vol. 27, IEEE, Sep. 24–27, 2000, pp 391–394.

Mueller, William C., Arrhythmia Detection Program for an Ambulatory ECG Monitor, ISA, 1978, pp 81–85.

*Primary Examiner*—Angela D. Sykes
*Assistant Examiner*—Kristen Mullen
(74) *Attorney, Agent, or Firm*—Michael C. Soldner; Girma Wolde-Michael

(57) ABSTRACT

A method and apparatus for method for discriminating heart rhythms includes computing a first predetermined number of RR intervals from received QRS intervals, and computing a median RR interval corresponding to a predetermined number of the first predetermined number of RR intervals. A predetermined beat-to-beat variation and a corresponding predetermined count are determined based on the computed median RR interval. Beat-to-beat variation differences between the first predetermined number of RR intervals are computed and a determination is made as to whether the computed beat-to-beat variation differences are greater than the predetermined beat-to-beat variation, and as to whether a number of the computed beat-to-beat variation differences that are greater than the predetermined beat-to-beat variation is greater than the predetermined count. The heart rhythm is identified as an irregular rhythm in response to the number being greater than or equal to the predetermined count.

16 Claims, 11 Drawing Sheets

U.S. PATENT DOCUMENTS

| | | | |
|---|---|---|---|
| 5,217,021 A | 6/1993 | Steinhaus et al. | 128/702 |
| 5,226,425 A | 7/1993 | Righter | 128/710 |
| 5,257,621 A * | 11/1993 | Bardy et al. | 607/5 |
| 5,289,824 A | 3/1994 | Mills et al. | 128/696 |
| 5,311,874 A | 5/1994 | Baumann et al. | 128/705 |
| 5,312,441 A | 5/1994 | Mader et al. | 607/5 |
| 5,312,446 A | 5/1994 | Holschbach et al. | 607/9 |
| 5,313,953 A | 5/1994 | Yomtov et al. | 128/696 |
| 5,333,616 A | 8/1994 | Mills et al. | 128/696 |
| 5,339,824 A | 8/1994 | Engira | 128/712 |
| 5,342,402 A | 8/1994 | Olson et al. | 607/5 |
| 5,365,935 A | 11/1994 | Righter et al. | 128/710 |
| 5,411,031 A | 5/1995 | Yomtov | 128/706 |
| 5,417,717 A | 5/1995 | Salo et al. | 607/18 |
| 5,511,553 A | 4/1996 | Segalowitz | 128/696 |
| 5,513,645 A | 5/1996 | Jacobson et al. | 128/710 |
| 5,518,001 A | 5/1996 | Snell | 128/697 |
| 5,591,215 A | 1/1997 | Greenhut et al. | 607/14 |
| 5,645,570 A * | 7/1997 | Corbucci | 607/5 |
| 5,749,900 A | 5/1998 | Schroeppel et al. | 607/4 |
| 5,779,645 A | 7/1998 | Olson et al. | 600/518 |
| 5,855,593 A * | 1/1999 | Olson et al. | 607/9 |
| 5,908,392 A * | 6/1999 | Wilson et al. | 600/509 |
| 5,913,550 A | 6/1999 | Watanuki | 29/603.1 |
| 5,941,831 A | 8/1999 | Turcott | 600/515 |
| 5,987,352 A | 11/1999 | Klein et al. | 600/509 |
| 5,991,656 A | 11/1999 | Olson et al. | 607/4 |
| 6,141,581 A | 10/2000 | Olson et al. | 600/515 |
| 6,230,059 B1 | 5/2001 | Duffin | 607/60 |
| 6,236,882 B1 | 5/2001 | Lee et al. | 600/509 |
| 6,275,732 B1 | 8/2001 | Hsu et al. | 607/14 |
| 6,308,095 B1 | 10/2001 | Hsu et al. | 600/518 |
| 6,317,632 B1 * | 11/2001 | Krig et al. | 607/14 |
| 6,567,691 B1 * | 5/2003 | Stadler | 600/515 |
| 6,718,197 B1 * | 4/2004 | Carlson et al. | 600/515 |

\* cited by examiner

| Rate | ΔRR | N |
|---|---|---|
| > 500 ms | 50 ms | 8 |
| (400 ms, 500 ms] | 25 ms | 8 |
| (320 ms, 400 ms] | 15 ms | 5 |
| < 320 ms | 15 ms | 5 |

Figure 7

METHOD AND APPARATUS FOR DISCRIMINATION ATRIAL FIBRILLATION USING VENTRICULAR RATE DETECTION

RELATED APPLICATIONS

A portion of this application claims priority and other benefits from U.S. Provisional Patent Application Ser. No. 60/253,553, filed Nov. 28, 2000, entitled "METHODS FOR DISCRIMINATION BETWEEN SINUS ARRYTHMIA AND AF USING VENTRICULAR RATE—DETECTION OF AF".

FIELD OF THE INVENTION

The present invention relates generally to detection of atrial fibrillation in implantable medical devices, and more particularly to a method and apparatus for discriminating atrial fibrillation from sinus arrhythmia and premature ventricular contractions using ventricular rate variability.

BACKGROUND OF THE INVENTION

A variety of techniques have been developed for collecting and interpreting data concerning the electrical activity of the heart using external medical devices (EMDs) both in the clinical setting, using portable external monitors worn by an ambulatory patient, or outside the clinical setting, using implantable medical devices (IMDs) implanted in an ambulatory patient to collect data relating to electrical heart function during daily activities of the patient. Such techniques include electrocardiography, vectorcardiography and polarcardiography.

The cardiac cycle as displayed in an ECG lead tracing reflects the electrical wave front as measured across an ECG lead, that is between two electrodes spaced apart on the patient's body, as shown in U.S. Pat. No. 4,587,976, for example. The portion of a cardiac cycle representing atrial depolarization is referred to as a "P-wave." Depolarization of the ventricular muscle fibers is represented by "Q", "R", and "S" points of a cardiac cycle. Collectively these "QRS" points are called an "R-wave" or a "QRS complex." Re-polarization of the depolarized heart cells occurs after the termination of another positive deflection following the QRS complex known as the "T-wave." The QRS complex is the most studied part of the cardiac cycle and is considered to be the most important for the prediction of health and survivability of a patient. However, the time relation of the P-wave to the QRS complex and the height and polarity of the T-wave and S-segment are also indicators of a healthy or diseased heart. The S-T segment of a healthy heart is usually isoelectric, i.e., neither positive nor negative in deflection from baseline of the ECG lead tracing. This S-T segment is a most important indicator of the health of the ventricular myocardium and is elevated in ischemia and due to infarctions disrupting the depolarization wave front.

The heart rate of the normal heart is governed by the atrial depolarization rate, which is regulated by the body's current requirement for cardiac output reflecting a level of physical exercise or stress. The normal cardiac cycle and heart rate is disrupted in many instances. Conduction defects affecting the A-V node response to a P-wave can cause the ventricles to beat too slowly, that is exhibit bradycardia, and not provide sufficient cardiac output. Other conduction defects and/or disease processes can cause the atria and/or ventricles to spontaneously depolarize at a rapid rate that, that is to exhibit a tachyarrhythmia, that is unrelated to the need for cardiac output, but diminishes or disrupts cardiac output. Such ventricular tachyarrhythmias include ventricular tachycardia (VT), ventricular fibrillation (VF) and ventricular flutter (VFl), and atrial tachyarrhythmias include atrial tachycardia (AT), atrial fibrillation (AF) and atrial flutter (AF).

In AF, the atria depolarize at an elevated rate that is highly irregular, and the atrial depolarizations are typically conducted intermittently to the ventricles, so that the ventricles beat synchronously at times and asynchronously at other times with the atrial depolarizations. In AFl, the atria beat at an elevated rate that is highly regular, and a portion of the atrial depolarizations are typically conducted to the ventricles, whereby the ventricles beat synchronously with every second or third atrial depolarization. Thus, the ventricular heart rate can be in a normal range or elevated but regular during an AFl episode, whereas the ventricular heart rate can be in a normal range or elevated but irregular during an AF episode. Episodes of AF and AFl affect the atrial mechanical function and can have an effect on the ventricular heart rate that negatively affects cardiac output of the ventricles. These episodes are accompanied by faintness, syncope, and tachyarrhythmia palpitation symptoms and occur spontaneously and intermittently.

Moreover, at times, the atria prematurely contract due to depolarizations initiated at ectopic foci other than the SA Node in the atrium, referred to as Premature Atrial Contractions (PACs) or ectopic P-waves. These PACs can be conducted to the ventricles to result in a ventricular contraction or can, due to their amplitude, be mistakenly detected in the ventricles as an R-wave or a ventricular depolarization conducted from the AV node.

Similarly, the ventricles can also develop ectopic foci that intermittently cause a spontaneous depolarization wave front or Premature Ventricular Contractions (PVCs) or ectopic R-waves. Such PACs and PVCs and other arrhythmias can be visually identified by trained medical care providers in the PQRST segments displayed on ECG tracings, if they manifest in the clinical setting.

The ventricular heart rate is determined as a function of the interval between successive ventricular depolarizations each marked by the R-wave of the electrocardiogram (ECG) or electrogram (EGM), that is, the RR interval between successive detected R-waves. Generally, the time interval between successive R-waves is denoted as the RR interval, and the difference between successive RR intervals is denoted as the ΔRR interval. A rapid and regular or irregular ventricular heart rate can be a normal sinus rhythm (NSR) tracking the normal atrial heart rate or can be due to PVCs and/or PACS or conducted AF or AFl or due to VT or VF or VFl originating in the ventricles.

There are many instances where it is desirable to be able to diagnose intermittent spontaneous cardiac arrhythmias, particularly AF and AFl, in ambulatory patients. These episodes of AF and AFl are difficult if not impossible to be induced and observed by the physician in tests conducted in a clinic. There is a recognized need to improve the capability of detecting and distinguishing various types of atrial and ventricular tachyarrhythmias from NSR and one another, so that a drug therapy can be prescribed and so that the efficacy of a prescribed drug therapy can be assessed for efficacy.

For many years, such patients, as well as patients suffering other bradyarrhythmias and tachyarrhythmias, have been equipped with external ECG monitoring systems, e.g., the patient-worn, real time Holter monitors, that continuously sample the ECG from skin electrodes and record it over a certain time period. Then, the ECG data must be analyzed to locate evidence of an arrhythmia episode and its nature and characteristics from which a diagnosis can be made.

As described in commonly assigned U.S. Pat. No. 5,312,446 and in U.S. Pat. No. 4,947,858, both incorporated herein by reference, the externally worn ECG recorders have inherent limitations in the memory capacity for storing sampled ECG and EGM data. Cost, size, power consumption, and the sheer volume of data over time have limited real time external Holter monitors to recording 24-hour segments or recording shorter segments associated with arrhythmias that are felt by the patient who initiates storage.

The use of the externally worn Holter monitor coupled with skin electrodes is also inconvenient and uncomfortable to the patient. The skin electrodes can work loose over time and with movement by the patient, and the loose electrodes generates electrical noise that is recorded with the EGM signal and makes its subsequent analysis difficult. It has long been desired to provide an implantable monitor or recorder that is hardly noticeable by the patient and provides the capability of recording only EGM data correlated with an arrhythmia episode that is automatically detected.

Over the last 40 years, a great many IMDs have been clinically implanted in patients to treat cardiac arrhythmias and other disorders including implantable cardioverter/defibrillators (ICDs) and pacemakers having single or dual chamber pacing capabilities, cardiomyostimulators, ischemia treatment devices, and drug delivery devices. Recently developed implantable pacemakers and ICDs employ sophisticated atrial and/or ventricular tachyarrhythmia detection criteria based on heart rate, rate stability and onset and/or the morphology and other characteristics of the atrial and/or ventricular EGM. Most of these ICDs employ electrical leads bearing bipolar electrode pairs located adjacent to or in an atrial and/or ventricular heart chamber for sensing a near field EGM or having one of the electrodes located on the ICD housing for sensing a far field, unipolar EGM. In either case, the near field or far field EGM signals across the electrode pairs are filtered and amplified in sense amplifiers coupled thereto and then processed for recording the sampled EGM or for deriving atrial and/or ventricular sense event signals from P-waves and/or R-waves of the EGM.

The atrial sense event signals are typically generated by atrial sense amplifiers when the P-wave amplitude exceeds an atrial sense threshold. Similarly, the ventricular sense event signals are typically generated by ventricular sense amplifiers when the R-wave amplitude exceeds a ventricular sense threshold. The ventricular heart rate is typically derived from the measured RR interval between successive ventricular sense event signals.

In current ICDs providing a therapy for treating a cardiac arrhythmia, the sense event signals and certain aspects of the sampled EGM waveform are utilized to automatically detect a cardiac bradyarrhythmia or tachyarrhythmia in one or more heart chamber and to control the delivery of an appropriate therapy in accordance with detection and therapy delivery operating algorithms. In such cardiac ICDs providing pacing or cardioversion/defibrillation therapies, both analog and digital signal processing of the EGM is continuously carried out to sense the P-wave and/or R-wave events and to determine when a cardiac arrhythmia episode occurs. For example, a digital signal processing algorithm is employed to distinguish various atrial and ventricular tachyarrhythmias from one another.

However, the expense and risk from implanting an intracardiac lead and/or a pacemaker with special monitoring functions, such as the utilization of a sense amplifier, is something both patients and physicians would prefer to avoid.

Implantable cardiac monitors have also been developed and clinically implanted that employ the capability of recording cardiac EGM data for subsequent interrogation and uplink telemetry transmission to an external programmer for analysis by a physician. The recorded data is periodically telemetered out to a programmer operated by the medical care provider in an uplink telemetry transmission during a telemetry session initiated by a downlink telemetry transmission and receipt of an interrogation command.

The MEDTRONIC® Reveal™ insertable loop recorder is a form of implantable monitor that is intended to be implanted subcutaneously and has a pair of sense electrodes spaced apart on the device housing that are used to pick up the cardiac far field EGM which in this case is also characterized as a "subcutaneous ECG". The Reveal™ insertable loop recorder samples and records one or more segment (depending on the programmed operating mode) of such far field EGM or subcutaneous ECG signals when the patient feels the effects of an arrhythmic episode and activates the recording function by applying a patient activator over the site of implantation. For example, the storage of a programmable length segment of the EGM can be initiated when the patient feels faint due to a bradycardia or tachycardia or feels the palpitations that accompany certain tachycardias. The memory capacity is limited, and so the segments of such EGM episode data that are stored in memory can be written over with new EGM episode data when the patient triggers storage and the memory is full. The most recently stored segment or segments of episode data is transmitted via an uplink telemetry transmission to an external programmer when a memory interrogation telemetry session is initiated by the physician or medical care provider using the programmer. Aspects of the Reveal™ insertable loop recorder are disclosed in commonly assigned PCT publication WO98/02209 and in U.S. Pat. No. 6,230,059.

Other examples of external monitoring devices include the Instromedics approach, seen in the Mills, et al patents (U.S. Pat. Nos. 5,333,616; 5,289,824 and 5,111,396) for a wrist worn monitor for ECG's which include features like patient triggering and microprocessor determination of event types (QRS detection). Wrist worn devices are also shown in the Righter patents issued to assignee Ralin, including U.S. Pat. Nos. 5,226,425 and 5,365,935. Jacobsen, et al in U.S. Pat. No. 5,513,645 describes multiple resolution storage for ECG's (ELA Medical is the assignee), and Snell's U.S. Pat. No. 5,518,001 vaguely describes a patient triggered recording device with multiple sensors and patient triggering(assigned to Pacesetter). InControl's approach is seen in the Yomatov patents, U.S. Pat. Nos. 5,411,031 and 5,313,953 which seems to concentrate on beat to beat timing records, suggests the use of an arrhythmia detector, and does mention the possibility of leadless electrodes for monitoring cardiac signals. Examples of an external monitor/recorders can be found in Segalowitz' patents, including U.S. Pat. No. 5,511,553, and Salo's U.S. Pat. No. 5,417,717. Another well known event recorder is the "King of Hearts" (.TM. of Instromedix) which records pre-event and post-event data.

Presently available pacemaker/cardioverter/defibrillator arrhythmia control devices, employ programmable fibrillation interval ranges and tachycardia detection interval ranges, along with measurement of suddenness of onset and rate variability. For future generations of devices, numerous detection and classification systems have been proposed.

Numerous patents, including U.S. Pat. No. 5,217,021 issued to Steinhaus et al., U.S. Pat. No. 5,086,772 issued to Larnard et al., U.S. Pat. No. 5,058,599 issued to Andersen and U.S. Pat. No. 5,312,441 issued to Mader et al. propose waveform morphology analysis systems for determining the type and origin of detected arrhythmias. Other patents, including U.S. Pat. No. 5,205,583 issued to Olson, U.S. Pat. No. 5,913,550 issued to Duffin, U.S. Pat. No. 5,193,535 issued to Bardy et al., U.S. Pat. No. 5,161,527 issued to Nappholz et al., U.S. Pat. No. 5,107,850 issued to Olive and U.S. Pat. No. 5,048,521, issued to Pless et al. propose systems for analysis of order and timing of atrial and ventricular events.

In the existing and proposed devices discussed above, one or two basic strategies are generally followed. A first strategy is to identify heart events, event intervals or event rates as they occur as indicative of the likelihood of the occurrence of specific types of arrhythmias, with each arrhythmia having a preset group of criteria that must be met as precedent to detection or classification. As events progress, criteria for identifying the various arrhythmias are all monitored simultaneously, with the first set of criteria to be met resulting in detection and diagnosis of the arrhythmia. A second strategy is to define a set of criteria for events, event intervals and event rates which is generally indicative of a group of arrhythmias, and following those criteria being met, analyzing preceding or subsequent events to determine which specific arrhythmia is present. An arrhythmia detection and classification system generally as disclosed in U.S. Pat. No. 5,342,402, issued to Olson et al., incorporated herein by reference in its entirety, uses both strategies together.

In certain ones of these cardiac monitoring devices, recording of EGM episode data is triggered by the patient. However, in many cases patients are either unaware of "silent" cardiac arrhythmias or are asleep or fail to activate the recording function when they recover from syncope (i.e., have fainted) when bradycardias and tachyarrhythmias occur, and so the accompanying EGM episode data is not recorded. It is therefore desirable to be able to automatically detect an arrhythmia and to initiate recording of the EGM data without having to rely upon the patient as disclosed in the above-incorporated '966 patent. On the other hand, the subcutaneous location environment of the sense electrode pair or pairs on the device housing is relatively noisy due to electromyographic signals generated by adjacent muscle groups that are exercised by the patient. Limb and trunk movements or even breathing can generate noise spikes that are superimposed upon the far field EGM signal and can make it appear to reflect a higher heart rate than the actual heart rate.

While the electromyographic noise level is not as pronounced in relation to the EGM signal level when bipolar sense electrode pairs located in or close by the atrium and ventricle are employed, as is typically the case with bipolar implantable pacemakers and ICDs, so that it is usually possible to filter out such noise in the sense amplifiers of such IMDs, when a cardiac monitoring device that does not include an atrial lead and a sense amplifier is utilized, the only means for reducing the effects of noise is to instruct the patient to assume a quiet body state when he/she initiates recording. As a result, when a cardiac monitoring device that does not include an atrial lead and a sense amplifier is utilized, the ability to differentiate between normal sinus arrhythmia and atrial fibrillation, for example, is even more difficult.

Accordingly, what is needed is a method and apparatus for improving the detection of atrial fibrillation in a cardiac monitoring device that does not utilize an atrial lead and/or atrial sense amplifier.

SUMMARY OF THE INVENTION

The present invention is directed toward an implantable medical device that takes differences in ventricular rate variability into account to discriminate between sinus arrhythmia and atrial fibrillation by computing the variation in beat-to-beat variation differences of RR intervals corresponding to a heart rhythm of a patient. According to a preferred embodiment, the present invention includes sensing means for sensing cardiac activity of a patient, first detector means for differentiating arrhythmias in response to differences in ventricular rate variability in the sensed cardiac activity and outputting a signal in response to the differentiated arrhythmias, and trigger means for receiving the signal from the detector means and initiating storage of the sensed cardiac activity.

In a preferred embodiment, the present invention computes a first predetermined number of RR intervals from received QRS intervals, and computes a median RR interval corresponding to a predetermined number of the first predetermined number of RR intervals. A predetermined beat-to-beat variation and a corresponding predetermined count associated with the computed median RR interval are determined. Beat-to-beat variation differences between the first predetermined number of RR intervals are computed, and a determination is made as to whether the computed beat-to-beat variation differences are greater than the predetermined beat-to-beat variation. A determination is then made as to whether a number of the computed beat-to-beat variation differences that are greater than the predetermined beat-to-beat variation is greater than the predetermined count, and the heart rhythm is identified as an irregular rhythm in response to the number being greater than or equal to the predetermined count.

BRIEF DESCRIPTION OF THE DRAWINGS

The features of the present invention which are believed to be novel are set forth with particularity in the appended claims. The invention, together with further objects and advantages thereof, may best be understood by making reference to the following description, taken in conjunction with the accompanying drawings, in the several figures of which like reference numerals identify like elements, and wherein:

FIG. 7 is a table for determining differences in rate variabilities in accordance with the present invention.

DETAILED DESCRIPTION OF THE PREFERRED EMBODIMENTS

Figure 1:
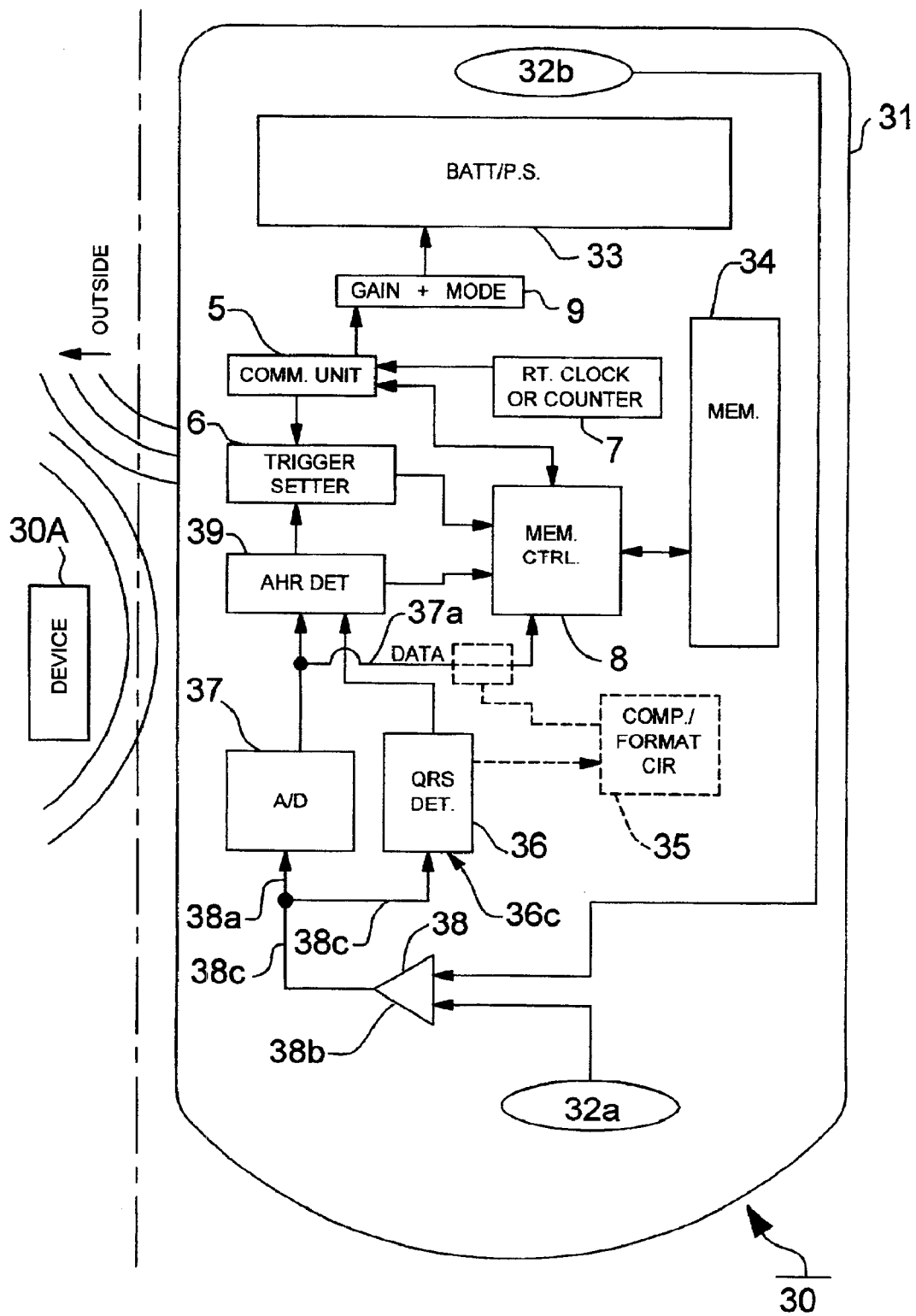
FIG. 1 is a functional schematic diagram of an implantable medical device according to a preferred embodiment of the present invention.

FIG. 1 is a functional schematic diagram of an implantable medical device according to a preferred embodiment of the present invention. This diagram should be taken as exemplary of the type of device in which the invention may be embodied, and not as limiting, as it is believed that the invention may usefully be practiced in a wide variety of device implementations, including devices providing therapies for treating atrial arrhythmias instead of or in addition to ventricular arrhythmias, cardioverters and defibrillators which do not provide anti-tachycardia pacing therapies, anti-tachycardia pacers which do not provide cardioversion or defibrillation, and devices which deliver different forms of anti-arrhythmia therapies such as nerve stimulation or drug administration.

As illustrated in FIG. 1, an implantable medical device 30 according to the present invention includes an implantable device shell 31, with electrodes 32a and 32b transmitting a signal from the body of the patient to an input mechanism 38, here drawn as a differential amplifier for simplicity only, the output of which is fed to a QRS detector circuit 36 and an A/D converter circuit 37. Both QRS detector circuit 36 and A/D converter circuit 37 supply output to an arrhythmia detector circuit 39, which in this preferred embodiment supplies an autotrigger signal to a trigger setter circuit 6. Trigger setter circuit 6 triggers recording of physiologic signals from a patient, such as ECG signals, for example, within a memory 34 of implantable medical device 30. The data output from A/D converter circuit 37 may be converted, compressed, formatted and marked or reformulated if desired in a compression/format circuit 35 before the data is ready for input into memory 34. A memory control circuit 8 receives input from A/D converter circuit 37, with or without conversion and so forth from compression/format circuit 35, from the auto triggering determination circuit, i.e., arrhythmia detector circuit 39 (which may include input directly from the QRS detector if desired) as well as signals from trigger setter circuit 6.

Trigger setter circuit 6 may also be controlled by a communications unit 5 which operates to receive and decode signals from the outside of the implant 30 that are telemetered or otherwise communicated in by a user. Communications unit 5 communicates with memory control circuit 8 to request the offloading of memory data for analysis by an outside device, using an antenna or other transceiver device or circuitry (not shown) to communicate with an outside interrogator device 30A. A real time clock or counter circuit 7 reports the time since start or real time to the outside interrogator device 30A contemporaneously with a data offloading session so that the events recorded in memory 34 may be temporally pinpointed.

Alternatives to this overall design may be considered, for example by using a microprocessor to accomplish some or all of the functions of circuits 6, 8, 39, and 35 but it is believed that such a design will not provide the power and size savings taught by use of the preferred design. See FIG. 2 and accompanying description below for a microprocessor driven version.

Figure 2:
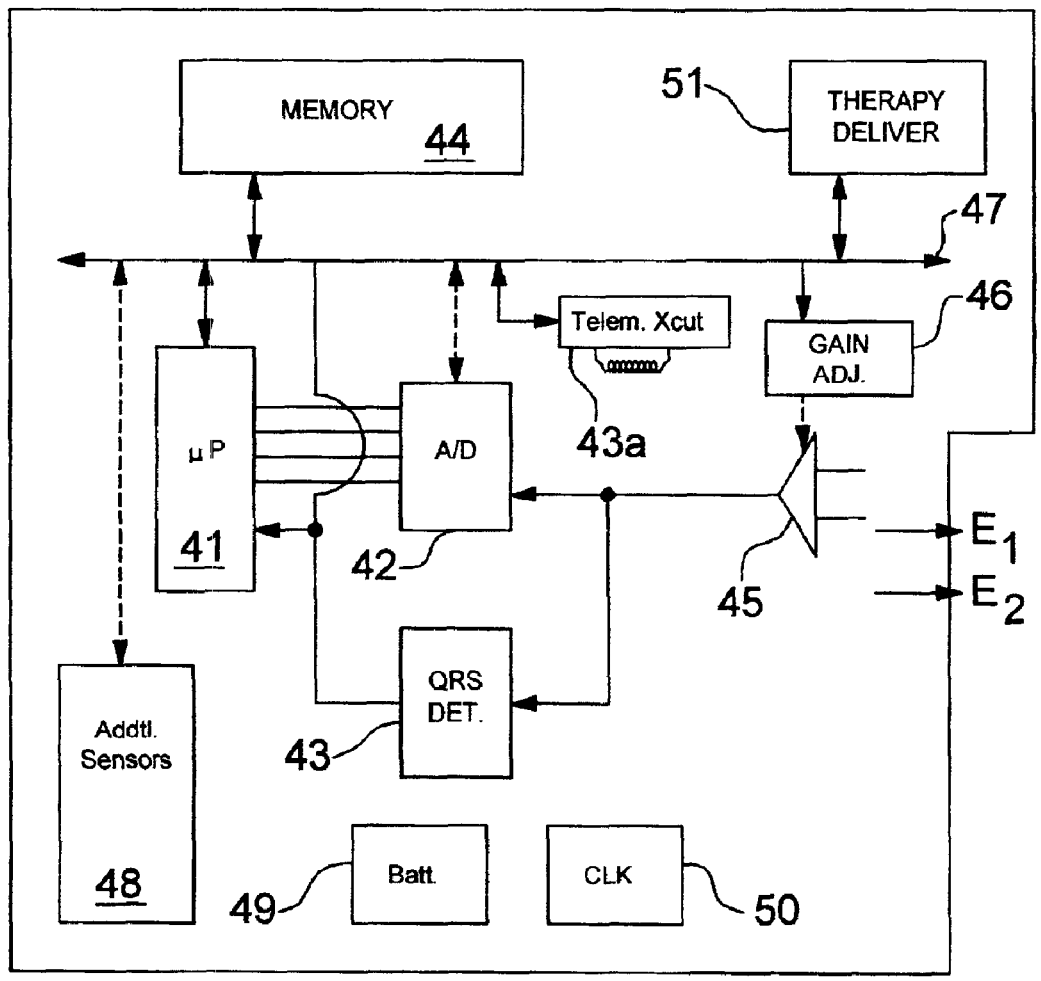
FIG. 2 is a schematic diagram of an implantable medical device according to an alternate preferred embodiment of the present invention.
Figures 2A, 2B, 2C:
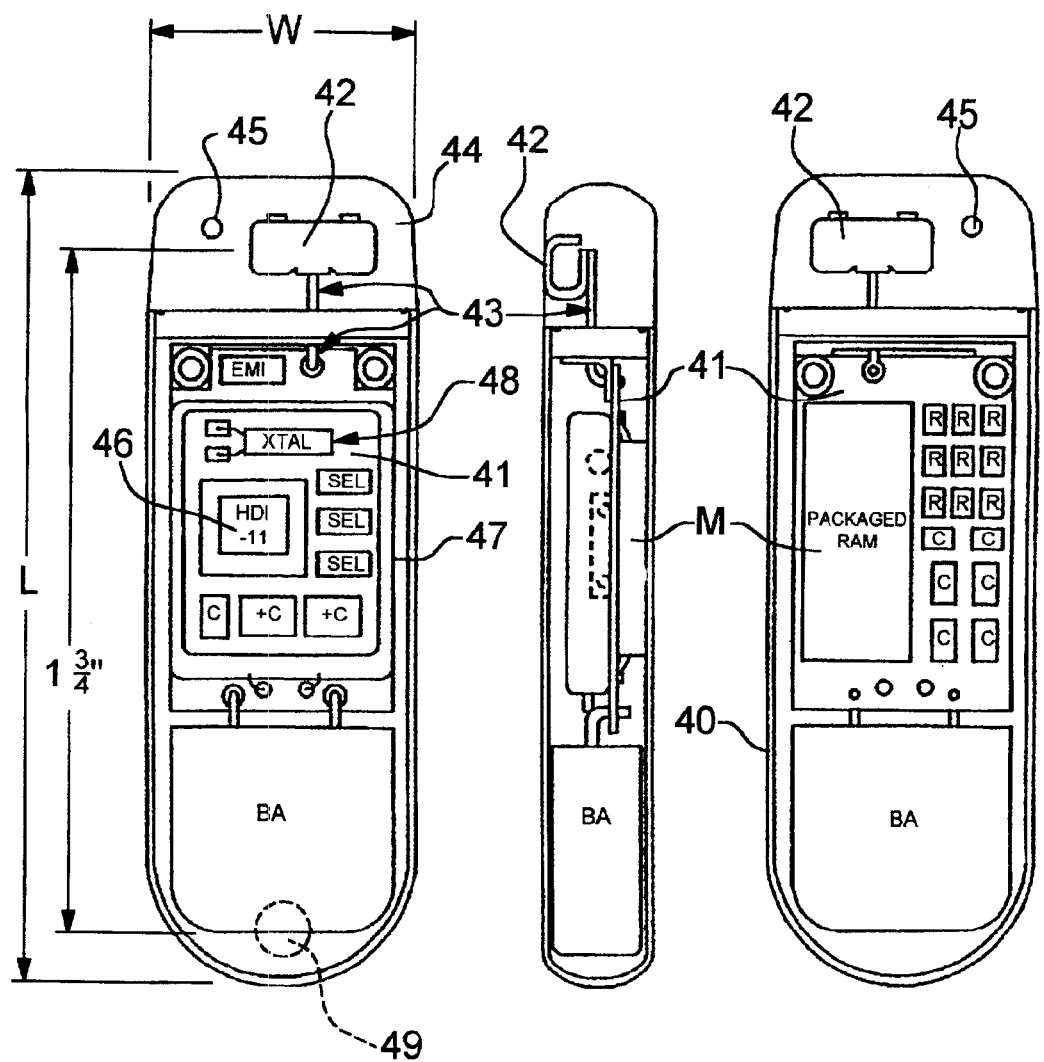
FIGS. 2A–2C are schematic diagrams of an implantable medical device according to the present invention.

FIGS. 2A–2C are schematic diagrams of an implantable medical device according to the present invention. As illustrated in FIGS. 2A–2C, an implantable medical device according to the present invention includes an outer titanium shell 40, in a plastic cap means 44, which together form the exterior of the device. The cap means 44 may be composed of material similar to those used for pacemaker connector blocks. Two electrodes, 42 and 49, provide metal surface contacts to the body of the patient. Electrode 49 is formed as a whole in a paralene coating over the metal body 40, of the device, and metal electrode 42 is connected via a feedthrough 43 which is itself electrically connected to a circuit board 41. Circuit board 41 contains all the electronics required for the device function and is connected to a battery BA for power. An integrated circuit 46 houses circuitry and intelligence required for functioning, and a memory M is packaged on an other side of circuit board 41. In this preferred form, the invention uses a communications circuit 48 having a telemetry antenna both to indicate from outside the body that a read out is requested of the device, and for communicating data out from said device. Programming of the device or mode setting will also use the communications circuit 48. In this form also a suture hole 45 is provided through the cap means 44. Electrode 49 is connected by a conductive connection (not shown in this FIG.) to circuit board 41. In this embodiment the length "1" is 2⅜" and "w" is "¾", however, these measurements can be varied within the constraints described. Electrode spacing here is about 1¾", center to center.

The exact sites of implant may advantageously be varied from patient to patient for various reasons apparent to the physician. Implant just under the skin now appears to provide the signal most free of skeletal muscle myopotential or body movement signal interference.

Referring again to FIG. 1, the external device 30A is preferably a device that is commonly called a "programmer" in the pacemaker art, because its usual function is to communicate with and program implanted devices. Software modifications and modifications to the telemetry system of device 30A to accommodate communication with and analysis of data from device 30 can be made as required. Such modifications will vary with the programmer type and are within the discretion of the manufacturer and thus will not be illustrated here. Using a programmer will avoid having to have additional devices cluttering the operating room or clinic by creating a separate and distinct external communications device for this invention. The functionality necessary for mere ECG monitoring and event triggering is minimal, so in the preferred embodiments that only monitor some form of ECG or other limited sensory input, a microprocessor can be and is done away with altogether by using particularized functional circuits instead of doing the functions in software.

FIG. 2 is a schematic diagram of an implantable medical device according to an alternate preferred embodiment of the present invention. As illustrated in FIG. 2, an implantable monitoring device 40 according to the present invention receives input from two electrodes $\epsilon_1$ and $\epsilon_2$ into an input amplifier 45. An analog signal output by amplifier 45 is converted to a digital signal by an A/D circuit 42 to provide a digital input data stream to a microprocessor 41. Additionally, a QRS detection circuit 43 receives and monitors the analog output of amplifier circuit 45 and provides an output signal to either microprocessor 41 or a bus 47 as desired. In this simplified device 40 in this schematic of FIG. 2, bus 47 provides a data conduit for enabling and disabling functions of all circuits that may be attached and for the transmission of data between the various circuits components and elements of the device 40. A telemetry transceiver 43a and memory circuit 44 will be able to move large amounts of data in a convenient way along this data conduit bus 47 as required for the operation of the system. Additional sensor circuits 48 may also provide data to the various circuits through the bus 47. A battery should be provided or other power circuit 49, and a clock circuit 50 would also be necessary to coordinate the transmission of data between the various circuit components and time their functions. Additionally, if desired, a therapy delivery circuit 51 may provide additional functions for the implanted medical monitoring device so that the device may take advantage of the data being gathered to deliver a particular therapy of use to the patient in a timely manner.

It believed to be most convenient to describe how the data is produced from the input signal with respect to the most preferred embodiment. However, it is also believed to be within the ambit of this invention to modify the following circuits for use with alternative embodiments such as the ones that may rely on a microprocessor controller circuit as in FIG. 2.

Figure 3A:
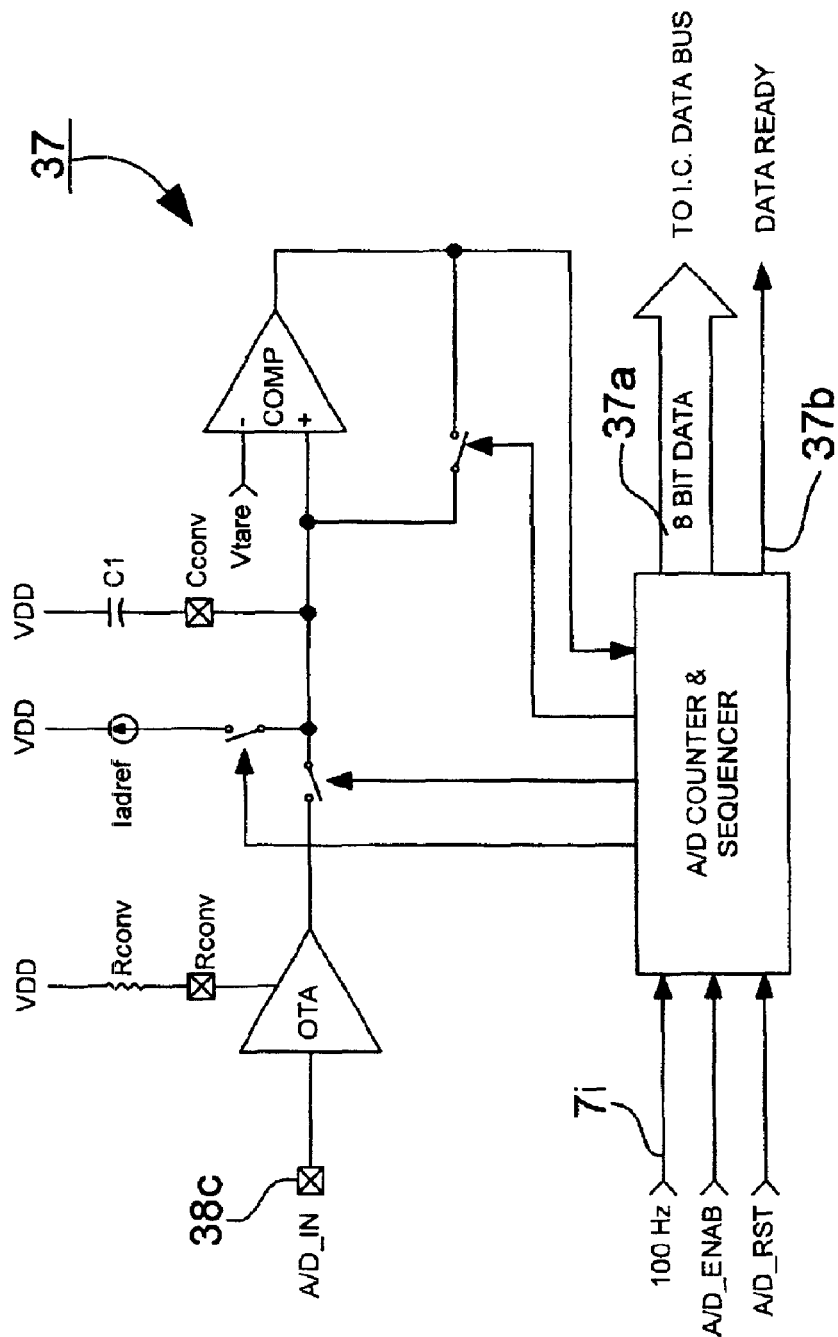
FIG. 3A is a block diagram of an analog to digital conversion circuit for monitoring and storing ECGs in a preferred embodiment of the present invention.

FIG. 3A is a block diagram of an analog to digital conversion circuit for monitoring and storing ECGs in a preferred embodiment of the present invention. As illustrated in FIGS. 1 and 3A, the clock input may advantageously use an output from real time clock/counter circuit 7 as input 7i. Input 38c is the analog input signal from input mechanism 38, and the converted output is a stream of 8 bit digital data words on a line 37a, sequenced by a timing line 37b.

Figure 3B:
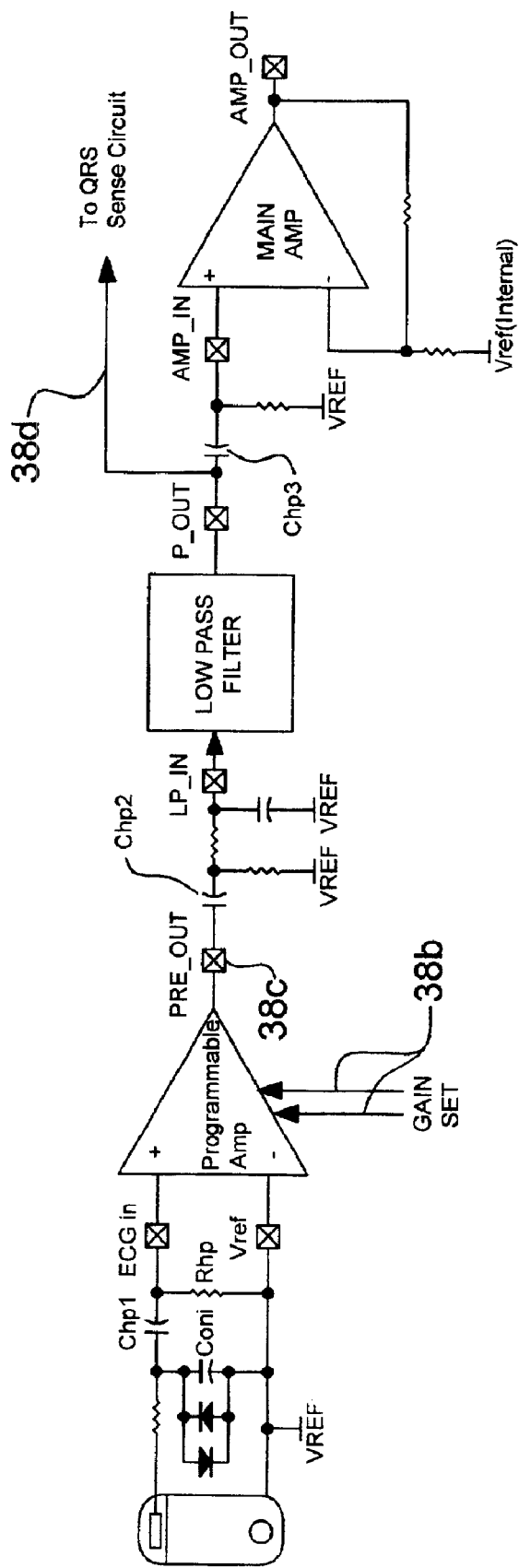
FIG. 3B is a block diagram of an input mechanism for monitoring and storing ECGs in a preferred embodiment of the present invention.

FIG. 3B is a block diagram of an input mechanism for monitoring and storing ECGs in a preferred embodiment of the present invention. FIG. 3B illustrates the basic parts of input mechanism 38 according to a preferred embodiment off the present invention, additionally indicating the input of gain set bits which can modify the value of the output of the low noise bipolar amplifier for output at line 38c, the input to QRS detector circuit 36. According to a preferred embodiment of the present invention, QRS detection is done on the analog signal, advantageously saving more complex detection after digital conversion.

Figure 3C:
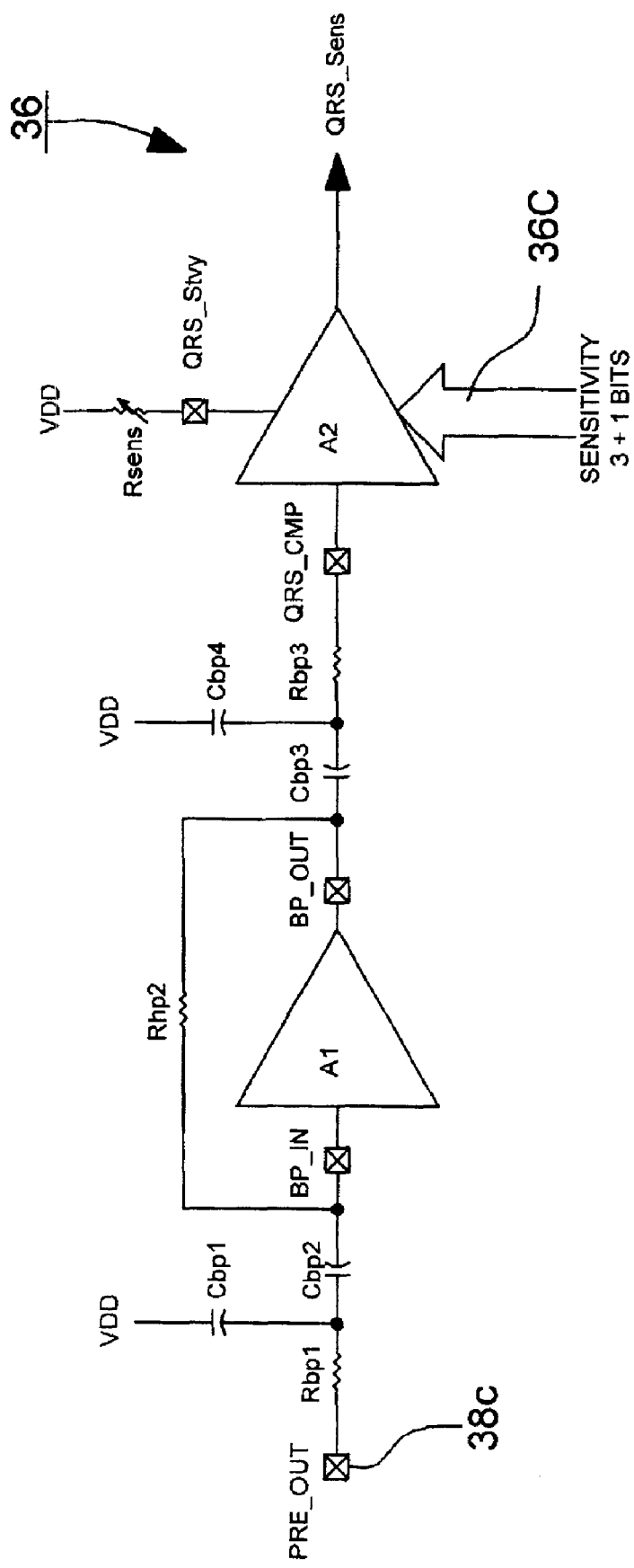
FIG. 3C is a block diagram of a QRS detector circuit for monitoring and storing ECGs in a preferred embodiment of the present invention.

FIG. 3C is a block diagram of a QRS detector circuit for monitoring and storing ECGs in a preferred embodiment of the present invention. As illustrated in FIG. 3C, QRS detector circuit 36 includes a 2nd order bandpass filter with a center frequency preferably in the 20–25 Hz range, having a transconductance amp A1, a summing amp/comparitor A2 and resistors Rbp1–3, capacitors Cbp1–4 and selectable resistor R sense connected as shown. R sense is preferably adjusted during manufacture. Additional control is provided for QRS sensitivity at line 36c, since the gain is selectable for this input.

Figure 3D:
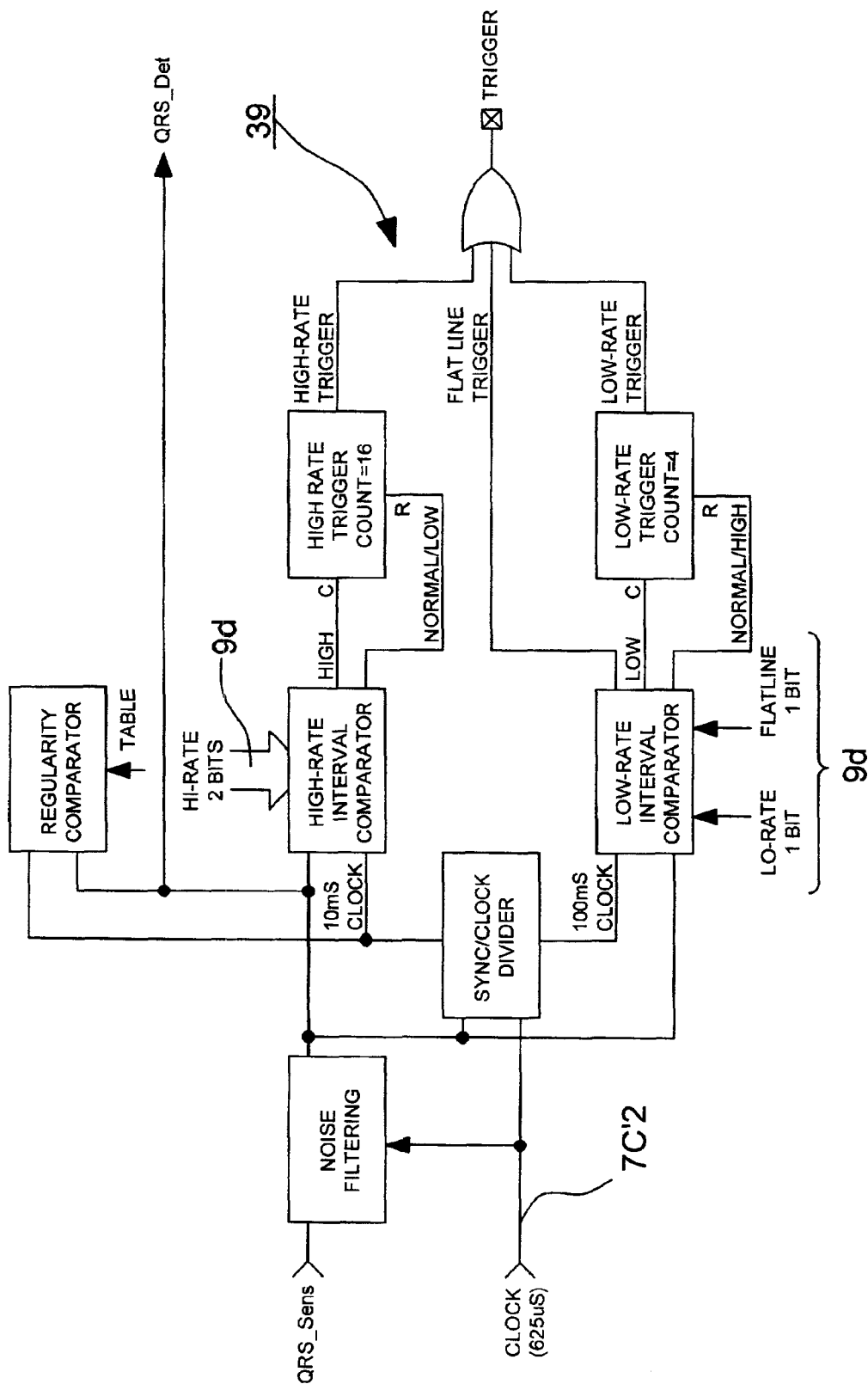
FIG. 3D is a block diagram of an arrhythmia detection circuit for monitoring and storing ECGs in a preferred embodiment of the present invention.

FIG. 3D is a block diagram of an arrhythmia detection circuit for monitoring and storing ECGs in a preferred embodiment of the present invention. As illustrated in FIG. 3D, arrhythmia detection circuit 39 includes an output that is monitored at a 200 millisecond blanking interval circuit, controlled by a clock input 7c'2. In a preferred embodiment, a high rate can be selected amongst four possible high rate values, with two selection bits dedicated to do so at input 9d and the low and flatline trigger rates each have one bit to turn them on or off provided by inputs 9d. These inputs designated 9d preferably come from a register that holds the gain, the mode, and the rate settings, illustrated as register 9 in FIG. 1. Such features may be programmable through communication with the implanted device by an external device. Preferred timing for the high rate triggers is 140, 162 and 182 beats per minute, requiring 8 consecutive beats at such a rate to initiate the trigger. However, the present invention could utilize seven or more settings, each requiring 8 to 32, and preferable around 16 or more consecutive beats at such a rate to initiate the trigger, as will be described below. Additionally the trigger may be programmed off. The low rate counter/comparitor may be programmable to detect low rates of 40 or 30 bpm, requiring 4 consecutive low rate intervals to trigger. Additionally a flat-line trigger can be set to occur after 3 or 4 and one half seconds of no QRS detection. For embodiments that include more sensors and/or electronics, additional sensors could be added to benefit the patient. One particularly useful would be an activity sensor based on a single or multi-axis accelerometer, which indicates the level of patient activity and his orientation. By checking for output that indicates the occurrence of a VVS (Vaso Vagal Syncope) episode, (for example, the patient falling from an episode) such an addition offers an improved trigger for events that might otherwise be missed by an arrhythmia detector set up like in FIG. 3D. Such a sensor trigger could replace the circuitry of 3D.

Additional circuits may be provided to support additional functions if desired, however in order to reduce size and power consumption and extend the life of the device and reduce the intrusion into the body of the wearer, auxiliary circuits should be kept to a minimum. Such additional circuits could support temperature sensing, oxygen sensing, pressure sensing, respiration sensing, and any other kind of sensing that can be demonstrated to have been known for implanted devices. They may each have their own auto triggers based on sensor output, or depend on manual triggers. In addition, activity sensing devices or positional sensing devices can provide additional input for recordation and/or autotriggerring functions. As new sensors become available they may also be incorporated into these designs.

In considering size, the maximum dimension of the device need be only the minimum required dimension for good signal to be obtained from the two electrode areas. In our studies we have found useable signal for ECG monitoring at a distance of about ½ inch (1 cm). The best minimum electrode distance for current electronics at reasonable prices appears to be from ¾ inches to 2 inches. Of course if the inventive features described herein are incorporated into a pacemaker or ICD, one could so, employing therapy delivering features of such devices in conjunction with the data recording features of the present invention.

The most important function of the simple versions of this invention is the long term ECG monitoring of the subcutaneous (or intramuscular) ECG. The device continuously records and monitors the subcutaneous ECG in an endless loop of memory. In its primary mode the device is triggered to save/retain in memory the last X minutes or seconds of ECG data by the patient subsequent to feeling symptoms of interest (e.g. syncope, palpitations, etc.).

In a preferred embodiment with 128K of memory, the device can store 42 or 21 minutes of ECG, which can be reset after offloading by telemetry to an external device for analysis and display. In one form there are four modes settable for patient trigger only and in another form there are autotriggers. In the patient only (also called "manual")

trigger modes, the patient can capture either one or three events between offloadings at either no compression or at a compression ratio of 1:2 or some other device supported ratio. When setting the mode of the implant, the physician or attendant can decide whether to record data in a compressed mode or not in the preferred embodiment. If greater detail of the triggered ECG is required than can be developed from compressed data storage, the physician should select non-compressed recording, thereby limiting the time available to record. In some embodiments sample rate may be modified as well, but this is not preferred.

Compression is preferably done using a known compression algorithm implemented in hardware. Many types are known and software compression could be used if desired too. An excellent and easy to implement example is found in the article Arrhythmia Detection Program for an Ambulatory ECG Monitor by Mueller, copyright 1978, ISA, ISBN 876645. Using this algorithm in one embodiment we have used a pre-trigger time of record of a maximum of 2400 seconds and a maximum post trigger record of 120 seconds, and at the higher sampled or less compressed rate of 1200/60 for a single event and 360/60 seconds for three events. These time values are obviously only examples and the reader can set whatever time he or his physician feels is appropriate within the ambit of this invention. After such a record is made the device memory locations are full and will be overwritten by the next triggered event since in the preferred embodiment the memory is maintained in a continuous loop.

Additional modes include those with pure autotriggering, which can mirror the patient triggered only modes if desired. It should be considered that with autotriggered events, the determination by the device of an event worth recording and the subsequent activation of the trigger by the device itself will be faster than the patient finding his device for activation or otherwise activating the device, so the pre trigger time record can be smaller. In one preferred embodiment the memory is segmented to allow for 14 autotriggers and 3 manual triggers. Further detail regarding modes is described with reference to FIGS. 4 and 5.

Figure 4:
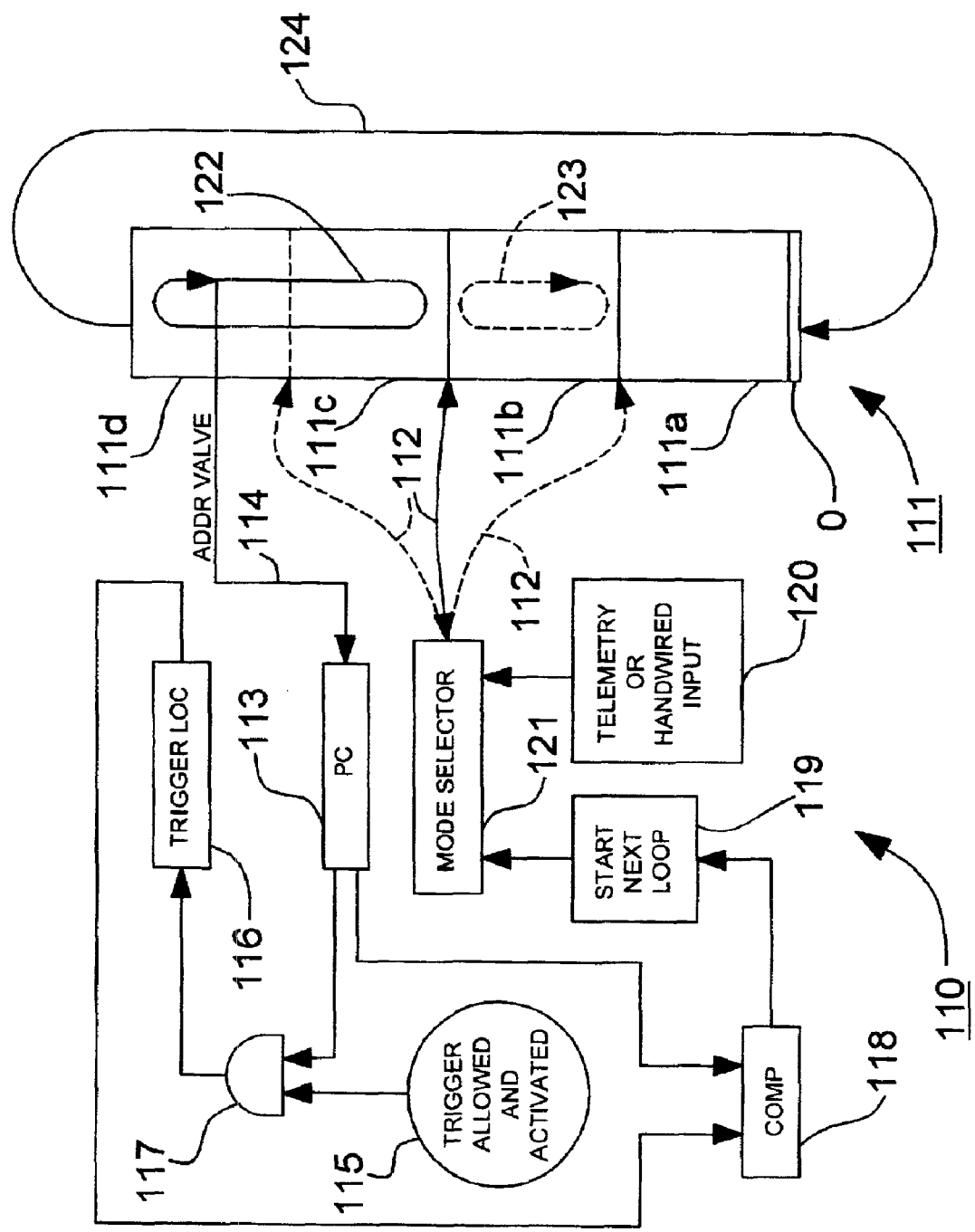
FIG. 4 is a block diagram of a looping memory and corresponding control circuitry according to a preferred embodiment of the present invention.

FIG. 4 is a block diagram of a looping memory and corresponding control circuitry according to a preferred embodiment of the present invention. As illustrated in FIG. 4, a memory 111 according to a preferred embodiment of the present invention is generally organized as a continuous loop of, preferably, 8 bit addresses starting at address 0 and looping back around to address 0 through line 124. By telemetry or hard-wired input during manufacture 120, a mode selector 121 is set so as to divide memory 111 into working segments 111a–d. The address of the start of each of these segments is indicated with lines 112.

Since this device is used for recording physiologic data, after the data is compressed, converted, formatted and is in appropriate digital form, it is continually recorded in memory 111. The address value at the tip of arrow 122 in the combined memory space 111d and memory space 111c is monitored by a program counter register 113. The size of each memory segment set in a given mode limits the amount of data available for each triggered event. In a preferred embodiment, using only one program counter set of registers, the flexibility to accommodate two different trigger lengths can be limited. Alternate forms of memory allocation are available. For example organizing the entire looping memory as one unit and marking each trigger would allow more flexibility but increase the overhead. See for example the memory structure in Enigra, U.S. Pat. No. 5,339,824, FIG. 7, incorporated herein by reference in its entirety.

To use a single program counter, the actual trigger address minus the time (in memory location storage events) required to have already stored the amount of data needed for pre-event analysis for that trigger is stored as a value in a trigger location register 116 of FIG. 4. If a larger time for pre-trigger recording is required by a trigger occurring during an already triggered event, (say, a manual trigger follows the occurrence of an auto trigger), the value in the trigger register can be decremented, thus yielding a larger pre-trigger time period in the allocated memory segment for this event. A priority system for whether to extend the pre-trigger record is simple to implement but again would require additional hardware and is not preferred. In fact the simplest construction ignores any new triggers once a trigger is set until the results of comparing the program counter with the trigger register corresponds to a match in value.

It is preferred to save more data for a manual triggered event than an auto triggered one because upon recovering from an event the patient has enough time to recover, get their wits about them, and find the triggering device. Manual triggering may therefore be set to record in double or multiple sized segments. Segments 111c and segment 111d of FIG. 4 are joined by looping arrow 122 to give effect to this concept.

Because the memory size is preferably quite limited a time record or first-in-first-out pool record should be kept on order that the newest triggers record only over the oldest events segments. An additional preferred feature allows for a mode that prevents recording over any triggered event segment. This is preferably implemented by a counter, which fills for each segment used and has storage for the set number of looping segments. When the counter is full, recording of new events stops.

When a trigger is activated and under the control program of the device is allowed, a signal 115 is permitted by some control gate 117 to allow the program counter address to be loaded into a trigger location address register 116. After loading, each subsequent clock cycle or set of clock cycles depending on the configuration of the device will load the trigger location from 116 into a comparator 118 to compare this location with the program counter address stored in register 113. When comparator 118 finds that they match, an appropriate output is generated to start the next loop via control circuit 119. Control circuit 119 will cause the mode selector to point to the next available loop location effectively placing that into the program counter 113.

Figure 5:
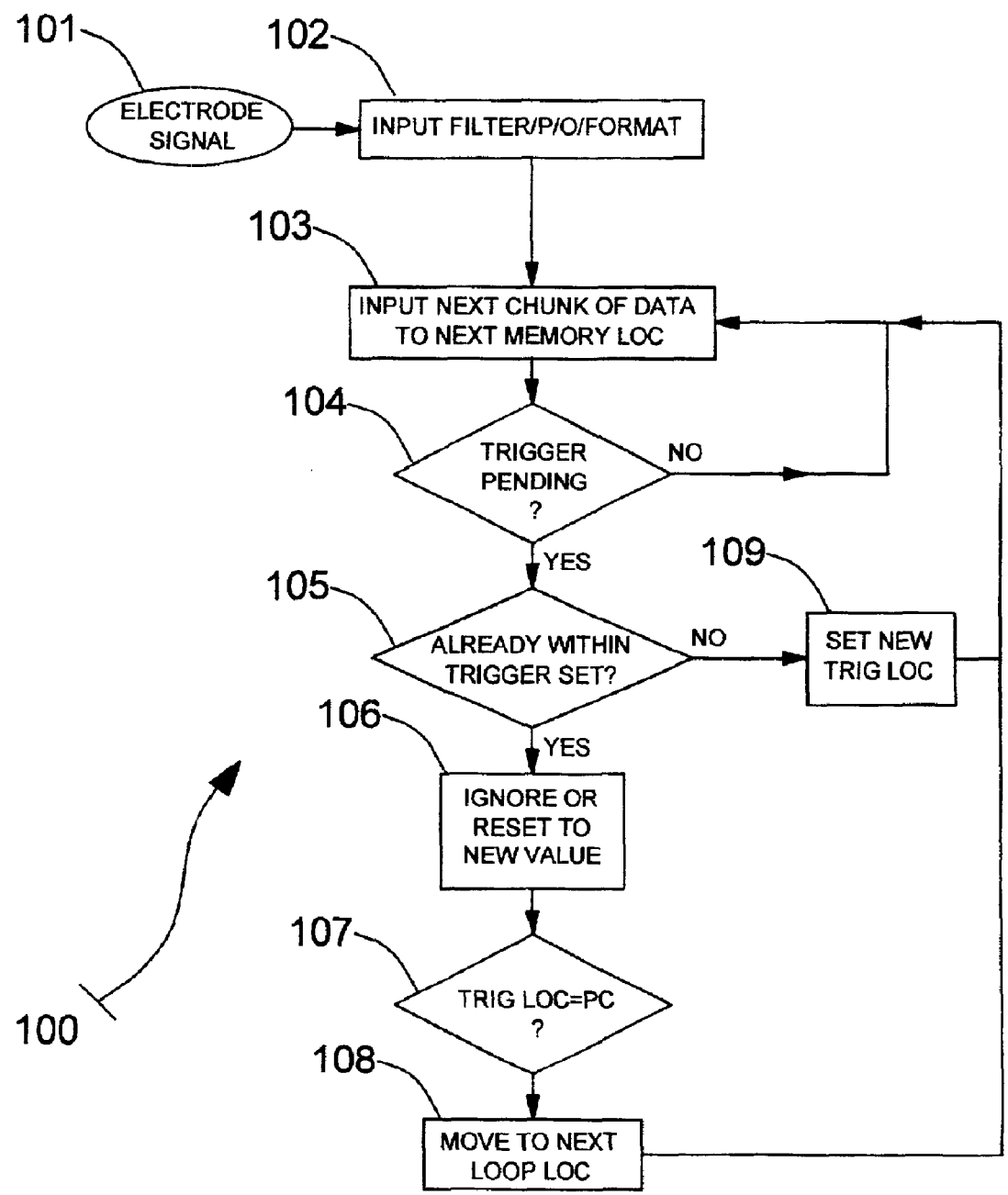
FIG. 5 is a flowchart of recordation of triggered events according to a preferred embodiment of the present invention.

FIG. 5 is a flowchart of recordation of triggered events according to a preferred embodiment of the present invention. As illustrated in FIG. 5, an electrode signal 101 is input filtered, converted from analog input to digital values, compressed and formatted if desired in step 102 so as to be in appropriate form to store in a memory location designated by a program counter pointer. This data word's form could be containing a value representing input signal compressed at various available ratios, and may be mixed with other information like data provided by another sensor or clock data. The data stored will of course carry information related to the signal taken at the sampling rate. Thus lower sampling rates to save power will adversely affect the usefulness or detail of the data. Whatever its preferred form, each data point stored as a word is referred to as a chunk.

Output from step 102 provides the next chunk of data to the next memory location in step 103. The implantable medical device checks to see if there is any trigger pending after storing each chunk of data in step 104. If not, the next chunk of data is stored. If there is a trigger pending, the device preferably checks to see if there is another trigger already set and if so either ignores it or resets the value of the reserved looping memory area (like areas 111a–d in FIG. 4) to accommodate a larger trigger or it ignores the trigger if it is smaller or if it indicates a smaller value needs to be stored. If on the other hand, no trigger is already set, then a new trigger location is recorded in the trigger location memory and then the next memory location is written with the next chunk of data. At step 107 if the trigger location is equal in value to the program counter, the device knows that it has gone through the entire loop reserved by the mode selector for this particular event record and then moves on to the next loop location, step 108.

Figure 6:
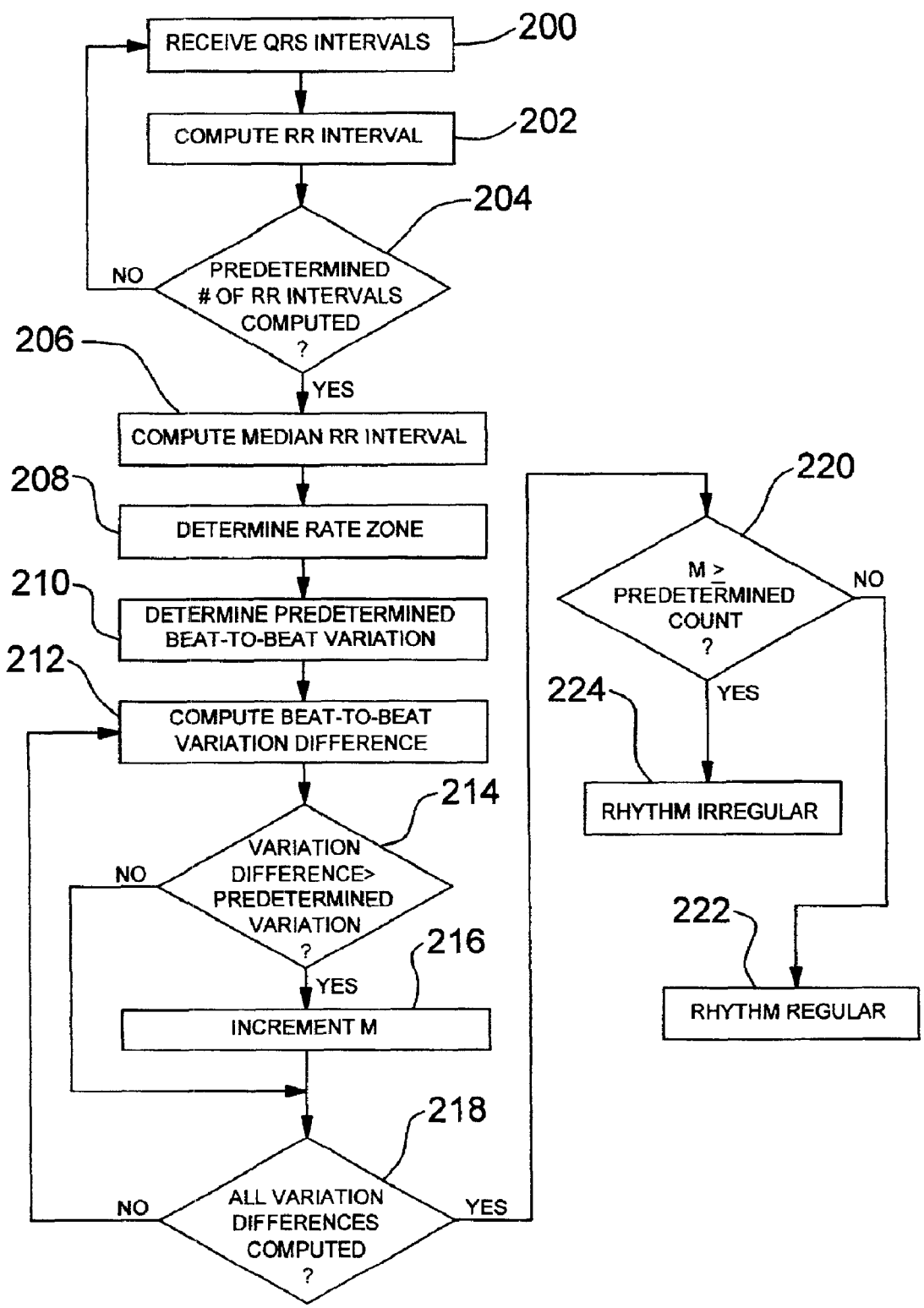
FIG. 6 is a flowchart of identification of a heart rhythm in an implantable medical device according to the present invention.

FIG. 6 is a flowchart of identification of a heart rhythm in an implantable medical device according to the present invention. As illustrated in FIGS. 1 and 6, arrhythmia detector 39 receives QRS intervals from QRS detector 36 corresponding to ventricular events detected by QRS detector 36, Step 200. An RR interval corresponding to the time interval between the R wave of a received QRS interval and the R wave of a previously received QRS interval is calculated for each received QRS interval, Step 202. Once a predetermined number of consecutive RR intervals have been calculated, Step 204, arrhythmia detector 39 computes a median RR interval associated with all or a portion of the predetermined number of consecutive RR intervals, Step 206. For example, according to a preferred embodiment of the present invention, once intervals between nineteen consecutive R waves has been calculated, resulting in eighteen RR intervals, a median RR interval associated with the last seven RR intervals of the eighteen RR intervals is calculated. It is understood that while a preferred embodiment of the present invention utilizes seven of eighteen consecutive RR intervals to compute the median RR interval, the present invention is not intended to be limited to the use of seven of eighteen consecutive RR intervals. Rather, the present invention may utilize any number of intervals between consecutive R waves to form any number of RR intervals in Steps 204 and 206. In addition, it is understood that the present invention may utilize any number of the RR intervals, including all of the RR intervals, to compute the median RR interval in Step 206.

FIG. 7 is a table for determining differences in rate variabilities in accordance with the present invention. As illustrated in FIG. 6, once the median RR interval has been computed in Step 206, a rate zone is determined based on the computed median RR interval, Step 208, so that an associated predetermined large beat-to-beat variation ($\Delta RR$ in FIG. 7) is defined, Step 210. In particular, using the table of FIG. 7, if the median RR interval computed in Step 206 is greater than 500 ms, the predetermined large beat-to-beat variation, $\Delta RR$, is approximately equal to 50 ms. If the median RR interval is greater than 400 ms but less than or equal to 500 ms, the predetermined large beat-to-beat variation, $\Delta RR$, is approximately equal to 25 ms. If the median RR interval is greater than 320 ms but less than or equal to 400 ms, the predetermined large beat-to-beat variation, $\Delta RR$, is approximately equal to 15 ms. Finally, if the median RR interval is less than or equal to 320 ms, the predetermined large beat-to-beat variation, $\Delta RR$, is approximately equal to 15 ms. In addition, a predetermined count (column N in FIG. 7) is associated with each median RR interval and predetermined large beat-to-beat variation, $\Delta RR$.

As illustrated in FIG. 6, once the rate zone has been determined using the table of FIG. 7 (Step 208), the corresponding predetermined large beat-to-beat variation, $\Delta RR$, is also determined from the table of FIG. 7, Step 210. For example, using the table of FIG. 7, if the median RR interval computed in Step 206 is 425 ms, the corresponding predetermined large beat-to-beat variation, $\Delta RR$, is determined to be 25 ms, while if the median RR interval computed in Step 206 is 350 ms, the corresponding predetermined large beat-to-beat variation, $\Delta RR$, is determined to be 15 ms, and so forth.

Once the predetermined large beat-to-beat variation, $\Delta RR$ from the table of FIG. 7 has been determined in Step 210, a beat-to-beat variation difference, $\Delta RR'$, is computed between consecutive RR intervals of the predetermined number of RR intervals, Step 212. For example, if the number of predetermined RR intervals calculated in Step 204 is equal to eighteen, so that there are eighteen consecutive RR intervals (N=18), an RR difference between each of the adjacent RR intervals is calculated by taking the difference of the absolute value of RR(n)–RR(n−1), resulting in seventeen (i.e., N−1) $\Delta'RRs$. For example, an RR difference is calculated between the first and the second RR interval, between the second and third RR interval, and so forth. Once the beat-to-beat variation difference, $\Delta'RR$ is computed between each consecutive ones of the predetermined number of RR intervals in Step 212, each resulting beat-to-beat variation difference, $\Delta'RR$ is compared to the predetermined large beat-to-beat variation, $\Delta RR$ from Step 210 and a determination is made as to whether the $\Delta'RR$ is greater than the predetermined large beat-to-beat variation, $\Delta RR$, Step 214. If the beat-to-beat variation difference, $\Delta'RR$ is greater than the predetermined large beat-to-beat variation, $\Delta RR$, a large variation number, M, corresponding to the number of the predetermined number of RR intervals from Step 204 (i.e., 18) that are greater than the predetermined large beat-to-beat variation, $\Delta RR$, is incremented, Step 216. If it is determined in Step 214 that the $\Delta'RR$ is not greater than the predetermined large beat-to-beat variation, $\Delta RR$, or once the large variation number M is incremented in Step 216, a determination is made as to whether a beat-to-beat variation difference, $\Delta'RR$, has been computed for each consecutive ones of the predetermined number of RR intervals, Step 218.

If a beat-to-beat variation difference, $\Delta'RR$, has not been computed for each consecutive ones of the predetermined number of RR intervals, the process returns to Step 212 so that a beat-to-beat variation difference, $\Delta'RR$, is computed for the next consecutive ones of the predetermined number of RR intervals, until a beat-to-beat variation difference, $\Delta'RR$, has been computed for each of the consecutive ones of the predetermined number of RR intervals, YES in Step 218.

Once a beat-to-beat variation difference, $\Delta'RR$, has been computed for each of the consecutive ones of the predetermined number of RR intervals, YES in Step 218, a determination is made in Step 220 as to whether M is greater than a predetermined count (column N in FIG. 7) associated with the median RR interval calculated in Step 202. For example, using the values described above, if the median RR interval computed in Step 206 is 425 ms, and therefore the corresponding predetermined large beat-to-beat variation, $\Delta RR$, is determined to be 25 ms, the predetermined count N is eight, while if the median RR interval computed in Step 206 is 350 ms, and the corresponding predetermined large beat-to-beat variation, $\Delta RR$, is determined to be 15 ms, the predetermined count N is five, and so forth.

If M is determined to be less than the associated predetermined count, the regularity criterion is considered to be satisfied and the associated rhythm is determined to be a regular rhythm, Step 222. On the other hand, if M is determined to be greater than or equal to the associated predetermined count, the regularity criterion is not considered to be satisfied and the associated rhythm is determined to be an irregular rhythm, Step 224. In this way the present invention computes the variation in the beat-to-beat variation difference, Δ'RR, between each consecutive ones of the predetermined number of RR intervals to determine whether the rhythm is a regular rhythm, or an irregular rhythm. Once a certain number of intervals are determined to be irregular rhythms, for example, once twelve of the last sixteen intervals are determined to be irregular, the rhythm is classified as atrial fibrillation. However, it is understood that the present invention is not limited to using twelve out of the last sixteen intervals to classify the rhythm as atrial fibrillation, but rather any number of intervals could be utilized to classify the rhythm.

The difference in ventricular rates between AF, sinus arrhythmia, and premature ventricular contractions (PVCs) is that the ventricular rate tends to be irregularly irregular, while for sinus arrhythmia and PVCs the ventricular rate tends to be regularly irregular. By computing the variation in the beat-to-beat variation difference, Δ'RR, the present invention therefore takes this difference in ventricular rate variability into account to discriminate between sinus arrhythmia and atrial fibrillation.

It is understood that while specific ranges are specified in the "range" column of the table in FIG. 7, along with specific corresponding beat-to-beat variations and predetermined counts in the "ΔRR" column and the "N" column respectively, it is understood that the present invention is not limited to those specific ranges and values. Rather, according to the present invention, the range column could include any number of ranges, with any given values being utilized for those ranges, and both the ΔRR column and the N column could include any values other than those shown as may be appropriate.

The preceding specific embodiments are illustrative of the practice of the invention. It is to be understood, therefore, that other expedients known to those of skill in the art or disclosed herein may be employed. In the following claims, means-plus-function clauses are intended to cover the structures described herein as performing the recited function and not only structural equivalents but also equivalent structures. For example, although a nail and a screw may not be structural equivalents in that a nail employs a cylindrical surface to secure wooden parts together, whereas a screw employs a helical surface, in the environment of fastening wooden parts, a nail and a screw are equivalent structures. It is therefore to be understood, that within the scope of the appended claims, the invention may be practiced otherwise than as specifically described without actually departing from the spirit and scope of the present invention.

What is claimed is:

1. A method for discriminating heart rhythms in an implantable medical device, comprising the steps of:
   receiving a QRS interval corresponding to the heart rhythm and computing a first predetermined number of RR intervals from the received QRS intervals;
   computing a median RR interval corresponding to a predetermined number of the first predetermined number of RR intervals;
   determining a rate zone in response to the computed median RR interval;
   determining a predetermined beat-to-beat variation corresponding to the rate zone;
   varying a count in response to the rate zone and the predetermined beat-to-beat variation;
   computing beat-to-beat variation differences between the first predetermined number of RR intervals;
   comparing the beat-to-beat variation differences to the predetermined beat-to-beat variation to determine whether the number of the computed beat-to-beat variation differences greater than the predetermined beat-to-beat variation is greater than the count; and
   identifying the heart rhythm in response to the number of the computed beat-to-beat variation differences relative to the count.

2. The method of claim 1, wherein the step of computing beat-to-beat variation differences comprises calculating the difference of the absolute value of RR(n)-RR(n-1), wherein RR(n) and RR(n-1) are consecutive RR intervals of the first predetermined number of RR intervals.

3. The method of claim 1, wherein the step of identifying comprises the steps of:
   identifying the heart rhythm as an irregular rhythm in response to the number of the computed beat-to-beat variation differences greater than the predetermined beat-to-beat variation being greater than or equal to the count; and
   identifying the heart rhythm as a regular rhythm in response to the number of the computed beat-to-beat variation differences greater than the predetermined beat-to-beat variation being less than the count.

4. The method of claim 3, wherein the irregular rhythm corresponds to atrial fibrillation.

5. The method of claim 1, wherein the predetermined beat-to-beat variation is set equal to 50 ms in response to the rate zone being greater than 500 ms, to 25 ms in response to the rate zone being less than or equal to 500 ms and greater than 400 ms, and to 15 ms in response to the rate zone being less than or equal to 400 ms.

6. The method of claim 5, wherein the count is set equal to 8 in response to the rate zone being greater than 400 ms and to 5 in response to the rate zone being less than or equal to 400 ms.

7. A method for discriminating between heart rhythms in an implantable medical device, comprising the steps of:
   computing a first predetermined number of RR intervals from received QRS intervals;
   computing a median RR interval corresponding to a predetermined number of the first predetermined number of RR intervals;
   determining a rate zone in response to the computed median RR interval;
   determining a predetermined beat-to-beat variation and varying a predetermined count in response to the rate zone and the predetermined beat-to-beat variation;
   computing beat-to-beat variation differences between the first predetermined number of RR intervals;
   determining whether the computed beat-to-beat variation differences are greater than the predetermined beat-to-beat variation; and
   determining whether a number of the computed beat-to-beat variation differences that are greater than the predetermined beat-to-beat variation is greater than the predetermined count;
   identifying the heart rhythm as an irregular rhythm in response to the number being greater than or equal to the predetermined count; and
   identifying the heart rhythm as a regular rhythm in response to the number being less than the predetermined count.

8. The method of claim 7, wherein the beat-to-beat variation differences are computed by taking the difference of the absolute value of RR(n)-RR(n-1), wherein RR(n) and RR(n-1) are consecutive RR intervals of the first predetermined number of RR intervals, and wherein the irregular rhythm corresponds to atrial fibrillation.

9. The method of claim 7, wherein the predetermined beat-to-beat variation is set equal to 50 ms in response to the rate zone being greater than 500 ms, to 25 ms in response to the rate zone being less than or equal to 500 ms and greater than 400 ms, and to 15 ms in response to the rate zone being less than or equal to 400 ms.

10. The method of claim 9, wherein the predetermined count is set equal 8 in response to the rate zone being greater than 400 ms and to 5 in response to the rate zone being less than or equal to 400 ms.

11. An implantable medical device, comprising:

sensing means for sensing cardiac activity of a patient;

first detector means for computing a median RR interval in response to a predetermined number of RR intervals associated with the sensed cardiac activity, determining a rate zone in response to the computed median RR interval, determining a variation associated with the determined rate zone, varying a count in response to the rate zone and the variation, computing variation differences between intervals of the predetermined number of intervals, determining whether the number of the computed variation differences that are greater than the determine variation is greater than the count, and outputting a signal in response to the determined number of the computed variation differences relative to the count; and trigger means for receiving the signal from the detector means and initiating storage of the sensed cardiac activity.

12. The device of claim 11, wherein the cardiac activity is determined to be an irregular rhythm in response to the number of the computed variation differences that are greater than the determined variation being greater than or equal to the count.

13. The device of claim 12, wherein the irregular rhythm corresponds to atrial fibrillation.

14. The device of claim 11, wherein the cardiac activity is determined to be a regular rhythm in response to the number of the computed variation differences that are greater than the determined variation being less than the count.

15. The device of claim 11, wherein the determined variation is set equal to 50 ms in response to the rate zone being greater than 500 ms, to 25 ms in response to the rate zone being less than or equal to 500 ms and greater than 400 ms, and to 15 ms in response to the rate zone being less than or equal to 400 ms.

16. The device of claim 15, wherein the count is set equal to 8 in response to the rate zone being greater than 400 ms and to 5 in response to the rate zone being less than or equal to 400 ms.

* * * * *